(12) United States Patent
Mehta (10) Patent No.: US 9,689,026 B2
(45) Date of Patent: *Jun. 27, 2017

(54) DETECTING SINGLE NUCLEOTIDE POLYMORPHISM USING OVERLAPPING HYDROLYSIS PROBES

(71) Applicant: Roche Molecular Systems, Inc., Pleasanton, CA (US)

(72) Inventor: Rochak Mehta, Union City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/232,070

(22) Filed: Aug. 9, 2016

(65) Prior Publication Data

US 2016/0340711 A1 Nov. 24, 2016

Related U.S. Application Data

(63) Continuation of application No. 14/555,343, filed on Nov. 26, 2014, now Pat. No. 9,441,268.

(51) Int. Cl.
*C07H 21/04* (2006.01)
*C12N 15/31* (2006.01)
*C12Q 1/68* (2006.01)

(52) U.S. Cl.
CPC .............. *C12Q 1/683* (2013.01); *C12Q 1/686* (2013.01); *C12Q 1/6818* (2013.01); *C12Q 1/6827* (2013.01); *C12Q 1/6848* (2013.01); *C12Q 1/6851* (2013.01)

(58) Field of Classification Search
None
See application file for complete search history.

(56) References Cited

U.S. PATENT DOCUMENTS

| 9,297,033 B2 | 3/2016 | Mehta |
| 9,441,268 B2 * | 9/2016 | Mehta ................ C12Q 1/6851 |
| 2014/0283197 A1 | 9/2014 | Bai et al. |

FOREIGN PATENT DOCUMENTS

| WO | 2008021446 A2 | 2/2008 |
| WO | 2013001005 A1 | 1/2013 |

OTHER PUBLICATIONS

Byrom M. et al, Exquisite allele discrimination by toehold hairpin primers, Nucleic Acids Research, Sep. 2, 2014, p. E120 (1-3), vol. 42, No. 15, Oxford University Press.
Huang S. et al., Thermodynamically modulated partially double-stranded linear DNA probe design for homogeneous real-time PCR, Nucleic Acids Research, Jan. 1, 2007, p. e101 (1-12), vol. 35, No. 16.
International Search Report issued Mar. 29, 2016 in Application No. PCT/EP2015/077466, 6 pages.
Kolpashchikov D.M. et al, An Elegant Biosensor Molecular Beacon Probe: Challenges and Recent Solutions, Scientifica, Jan. 1, 2012, p. E58 (1-17), vol. 32, No. 6, Hindawi Publishing Corporation.

* cited by examiner

*Primary Examiner* — James Martinell
(74) *Attorney, Agent, or Firm* — David J. Chang (57) ABSTRACT

Methods for the rapid detection of the presence or absence of a SNP in a target nucleic acid in a sample are described. The methods can include performing an amplifying step, a hybridizing step utilizing a double stranded probe with two overlapping SNP specific hydrolysis probe sequences where one of the probe sequences can include a hairpin structure toward the 3' end, and a detecting step. Furthermore, the double stranded SNP specific hydrolysis probes along with kits are provided that are designed for the detection of a SNP in a target nucleic acid.

15 Claims, 3 Drawing Sheets

SEQUENCE LISTING

```
<160> NUMBER OF SEQ ID NOS: 15

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (2)..(3)
<223> OTHER INFORMATION: Propynyl dC
<220> FEATURE:
<221> NAME/KEY: modified_base
<222> LOCATION: (6)..(6)
<223> OTHER INFORMATION: Propynyl dC
<220> FEATURE:
<221> NAME/KEY: modified_base
<222> LOCATION: (10)..(10)
<223> OTHER INFORMATION: Propynyl dC
<220> FEATURE:
<221> NAME/KEY: modified_base
<222> LOCATION: (12)..(13)
<223> OTHER INFORMATION: Propynyl dC
<220> FEATURE:
```

```
<221> NAME/KEY: modified_base
<222> LOCATION: (16)..(16)
<223> OTHER INFORMATION: Propynyl dC

<400> SEQUENCE: 1
accaacaagc gccgac                                                          16

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ttgttggtca accccgacgg gg                                                   22

<210> SEQ ID NO 3
<211> LENGTH: 14
<212> TYPE: RNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (2)..(2)
<223> OTHER INFORMATION: Propynyl dC
<220> FEATURE:
<221> NAME/KEY: modified_base
<222> LOCATION: (3)..(3)
<223> OTHER INFORMATION: Propynyl dU
<220> FEATURE:
<221> NAME/KEY: modified_base
<222> LOCATION: (5)..(6)
<223> OTHER INFORMATION: Propynyl dU
<220> FEATURE:
<221> NAME/KEY: modified_base
<222> LOCATION: (9)..(9)
<223> OTHER INFORMATION: Propynyl dC
<220> FEATURE:
<221> NAME/KEY: modified_base
<222> LOCATION: (11)..(11)
<223> OTHER INFORMATION: Propynyl dC
<220> FEATURE:
<221> NAME/KEY: modified_base
<222> LOCATION: (12)..(12)
<223> OTHER INFORMATION: Propynyl dU

<400> SEQUENCE: 3
acuguuggcg cugg                                                            14

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(2)
<223> OTHER INFORMATION: Propynyl dC
<220> FEATURE:
<221> NAME/KEY: modified_base
<222> LOCATION: (5)..(5)
<223> OTHER INFORMATION: Propynyl dC
<220> FEATURE:
<221> NAME/KEY: modified_base
<222> LOCATION: (9)..(9)
<223> OTHER INFORMATION: Propynyl dC
<220> FEATURE:
```

```
<221> NAME/KEY: modified_base
<222> LOCATION: (12)..(12)
<223> OTHER INFORMATION: Propynyl dC
<220> FEATURE:
<221> NAME/KEY: modified_base
<222> LOCATION: (14)..(14)
<223> OTHER INFORMATION: Propynyl dC

<400> SEQUENCE: 4
ccaacagtcg gcgc                                                        14

<210> SEQ ID NO 5
<211> LENGTH: 14
<212> TYPE: RNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (2)..(3)
<223> OTHER INFORMATION: Propynyl dC
<220> FEATURE:
<221> NAME/KEY: modified_base
<222> LOCATION: (4)..(4)
<223> OTHER INFORMATION: Propynyl dU
<220> FEATURE:
<221> NAME/KEY: modified_base
<222> LOCATION: (6)..(6)
<223> OTHER INFORMATION: Propynyl dC
<220> FEATURE:
<221> NAME/KEY: modified_base
<222> LOCATION: (10)..(10)
<223> OTHER INFORMATION: Propynyl dC
<220> FEATURE:
<221> NAME/KEY: modified_base
<222> LOCATION: (12)..(13)
<223> OTHER INFORMATION: Propynyl dC

<400> SEQUENCE: 5
accuacaagc gccg                                                        14

<210> SEQ ID NO 6
<211> LENGTH: 18
<212> TYPE: RNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(1)
<223> OTHER INFORMATION: Propynyl dC
<220> FEATURE:
<221> NAME/KEY: modified_base
<222> LOCATION: (2)..(3)
<223> OTHER INFORMATION: Propynyl dU
<220> FEATURE:
<221> NAME/KEY: modified_base
<222> LOCATION: (5)..(5)
<223> OTHER INFORMATION: Propynyl dU
<220> FEATURE:
<221> NAME/KEY: modified_base
<222> LOCATION: (9)..(10)
<223> OTHER INFORMATION: Propynyl dC
<220> FEATURE:
<221> NAME/KEY: modified_base
<222> LOCATION: (13)..(16)
<223> OTHER INFORMATION: Propynyl dC

<400> SEQUENCE: 6
cuuguaggcc aaccccga                                                    18
```

```
<210> SEQ ID NO 7
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gccagctgag ccaattcatg gtccagaaca acccgctgtc ggggttgacc aacaagcgcc    60
gactgtcggc gctggggtcc ggcgg                                          85

<210> SEQ ID NO 8
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gccagctgag cctattcatg gaccagaaca acccgctgca ggggttgacc cacaagcgcc    60
gactgttggc gctggggccc ggcgg                                          85

<210> SEQ ID NO 9
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gccagctgag ccaattcatg gaccagaaca acccgctgtc ggggttgacc cacaagcgcc    60
gactgtcggc gctggggccc ggcgg                                          85

<210> SEQ ID NO 10
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gccagctgag ccaattcatg gaccagaaca acccgctgtc ggggttgacc cacaagcgcc    60
gactgtcggc gctggggccc ggcgg                                          85

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
accaacaagc gccgac                                                    16

<210> SEQ ID NO 12
<211> LENGTH: 14
<212> TYPE: RNA
<213> ORGANISM: Artificial Sequence
<220> FEATURE:
<223> OTHER INFORMATION: Description of Artificial Sequence: Synthetic
```

```
              probe

<400> SEQUENCE: 12
acuguuggcg cugg                                                         14

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
ccaacagtcg gcgc                                                         14

<210> SEQ ID NO 14
<211> LENGTH: 14
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 14
accuacaagc gccg                                                         14

<210> SEQ ID NO 15
<211> LENGTH: 18
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 15
cuuguaggcc aaccccga                                                     18
```

DETECTING SINGLE NUCLEOTIDE POLYMORPHISM USING OVERLAPPING HYDROLYSIS PROBES

CROSS REFERENCE TO RELATED APPLICATIONS

This application is a continuation of U.S. patent application Ser. No. 14/555,343 filed on Nov. 26, 2014, which is hereby incorporated in its entirety by reference.

REFERENCE TO SEQUENCE LISTING

This application contains a Sequence Listing submitted as an electronic text file named "32320_US1_Sequence_Listing.txt", having a size in bytes of 6 kb, and created on Aug. 8, 2016. The information contained in this electronic file is hereby incorporated by reference in its entirety pursuant to 37 CFR §1.52(e)(5).

FIELD OF THE INVENTION

The present invention relates to the field of polymerase chain reaction (PCR) based diagnostic, and more particularly, to PCR detection methods utilizing overlapping hydrolysis probes.

BACKGROUND OF THE INVENTION

PCR is an efficient and cost effective way to copy or 'amplify' small segments of DNA or RNA. Using PCR, millions of copies of a section of DNA are made in just a few hours, yielding enough DNA required for analysis. This method allows clinicians to diagnose and monitor diseases using a minimal amount of sample, such as blood or tissue. Real-time PCR allows for amplification and detection to occur at the same time. One method of detection is done by utilizing oligonucleotide hydrolysis probes (also known as TaqMan® probes) having a fluorophore covalently attached, e.g., to the 5' end of the oligonucleotide probe and a quencher attached, e.g., internally or at the 3' end. Hydrolysis probes are dual-labeled oligonucleotide probes that rely on the 5' to 3' nuclease activity of Taq polymerase to cleave the hydrolysis probe during hybridization to the complementary target sequence, and result in fluorescent based detection.

Real time PCR methods can be used for amplifying and detecting sequence variations in target nucleic acids having single nucleotide polymorphism (SNP). However, many of the available SNP detection/genotyping assays are based on the assumption that the SNP is Malefic (see, e.g., Morita et al., Mol. Cel. Probes, 2007, 21, 171-176). Detection of SNP with currently existing real time PCR methods lacks sufficient sensitivity and specificity. Hydrolysis probes, such as standard TaqMan® probes, are typically designed to be about 18 to 22 bases in length in order to have 8-10° C. higher melting temperature (Tm) as compared to the primer. Standard TaqMan® probes generally prove to be less specific and sensitive for SNP detection and fail to show complete discrimination between the WT (Wild-type) and the MT (Mutant) targets. Current TaqMan® based SNP genotyping assays involve the use of TaqMan® MGB (Minor Groove Binders) probes that are shorter in length with increased probe-template binding stability for allelic discrimination. Additional base modifications such as stabilizing bases (propynyl dU, propynyl dC) can also be included in standard TaqMan® probe design for improved SNP detection and discrimination. Thus there is a need in the art for a quick and reliable method to specifically detect SNPs in a sensitive manner.

SUMMARY OF THE INVENTION

The subject matter of the present disclosure includes double stranded SNP specific hydrolysis probes where both probe strands are SNP specific and overlap at the SNP location. In some embodiments, one of the probe strands is designed to include a hairpin structure toward the 3' end. The hairpin structure near the 3' end of the probe delays the hybridization of the 3' portion of the probe to the template and thus helps in the discrimination of the WT and the MT targets based on the single mismatch between the reporter and the quencher which is near the 5' end. The 5' portion of the SNP specific probe can hybridize more efficiently to the MT template as compared to the WT template. When the SNP specific probe finds the WT target, the single mismatch to the WT target can prevent hybridization and probe cleavage, and thus no fluorescence can be detected.

In one embodiment, a method for detecting a SNP in a target nucleic acid in a sample is provided, the method including performing an amplifying step including contacting the sample with a first primer having a first nucleic acid and a second primer having a second nucleic acid sequence to produce an amplification product including a sense strand and an anti-sense strand if any target nucleic acid is present in the sample; performing a hybridizing step including providing the amplification product with a double stranded probe including a first SNP specific hydrolysis probe having a third nucleic acid sequence complementary to a first SNP containing region of the sense strand, the first SNP specific hydrolysis probe including a first interactive label and a second interactive label, a first 5' end and a first 3' end; and a second SNP specific hydrolysis probe having a fourth nucleic acid sequence complementary to a SNP containing region of the anti-sense strand, the second SNP specific hydrolysis probe including a third interactive label and a fourth interactive label, a second 5' end and a second 3' end; and detecting the presence or absence of the amplification product, wherein the presence of the amplification products is indicative of the presence of the SNP in the target nucleic acid target, and wherein the absence of the amplification products is indicative of the absence of the SNP in the target nucleic acid target. In some embodiments, the second SNP specific hydrolysis probe can include a hairpin structure toward the second 3' end, the hairpin structure including a region of non-naturally occurring nucleic acid sequence including one or more additional nucleotides to produce the hairpin structure.

In another embodiment, a kit for detecting a SNP in a target nucleic acid in a sample is provided, the kit including a first primer having a first nucleic acid and a second primer having a second nucleic acid sequence specific to produce an amplification product including a sense strand and an anti-sense strand of a target nucleic acid; and a double stranded probe including a first SNP specific hydrolysis probe having a third nucleic acid sequence complementary to a first SNP containing region of the sense strand, the first SNP specific hydrolysis probe including a first interactive label and a second interactive label, a first 5' end and a first 3' end; and a second SNP specific hydrolysis probe having a fourth nucleic acid sequence complementary to a SNP containing region of the anti-sense strand, the second SNP specific hydrolysis probe including a third interactive label and a fourth interactive label, a second 5' end and a second 3' end.

In some embodiments, the second SNP specific hydrolysis probe can include a hairpin structure toward the second 3' end, the hairpin structure including a region of non-naturally occurring (e.g., changed or additional) nucleic acid sequence including one or more additional nucleotides to produce the hairpin structure.

In one embodiment, a double stranded probe is provided including a first SNP specific hydrolysis probe having a first nucleic acid sequence complementary to a first SNP containing region of the sense strand, the first SNP specific hydrolysis probe including a first interactive label and a second interactive label, a first 5' end and a first 3' end; and a second SNP specific hydrolysis probe having a second nucleic acid sequence complementary to a SNP containing region of the anti-sense strand, the second SNP specific hydrolysis probe including a third interactive label and a fourth interactive label, a second 5' end and a second 3' end. The first and the third interactive labels may be a donor fluorescent moiety toward, near, or at the 5' terminus of each probe strands, and the second and fourth interactive labels may be a corresponding acceptor fluorescent moiety, e.g., a quencher, for example, within no more than 8 nucleotides of the donor fluorescent moiety on each of the strands of the double stranded hydrolysis probe. In some embodiments, the second SNP specific hydrolysis probe can include a hairpin structure toward the second 3' end, the hairpin structure including a region of non-naturally occurring (e.g., changed or additional) nucleic acid sequence including one or more additional nucleotides to produce the hairpin structure.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Figure 1:
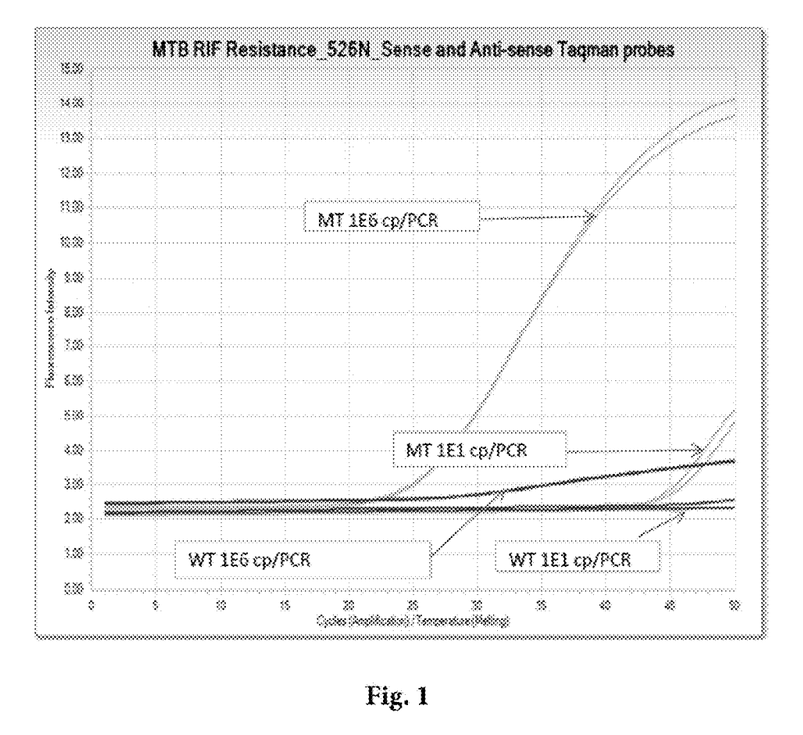
FIG. 1 shows real time PCR amplification curves for wild type and Mutant 526N SNP detection using a double stranded hydrolysis probe with both sense and antisense probe strands being SNP specific and the sense strand having a hairpin structure toward the 3' end.
Figure 2:
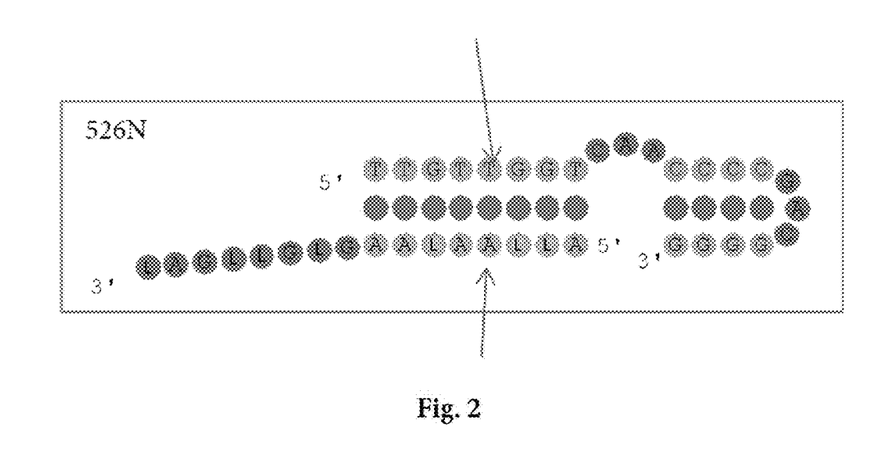
FIG. 2 shows a 526N SNP specific double stranded hydrolysis probe with both sense and antisense probe strands being SNP specific and the sense strand having a hairpin structure toward the 3' end.
Figure 3:
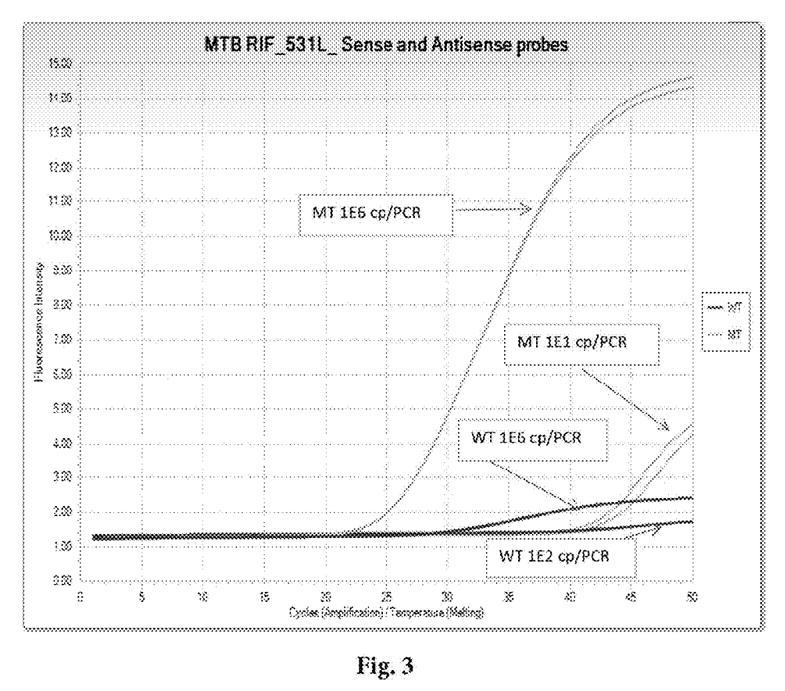
FIG. 3 shows real time PCR amplification curves for wild type and Mutant 531L SNP detection using a double stranded hydrolysis probe with both sense and antisense probe strands being SNP specific.
Figure 4:
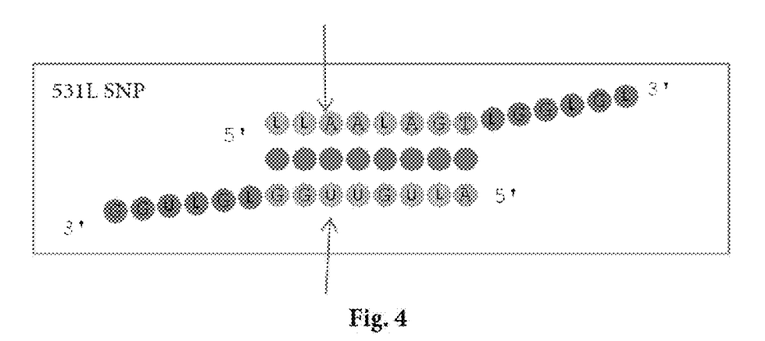
FIG. 4 shows a 531L SNP specific double stranded hydrolysis probe with both sense and anti-sense probe strands being SNP specific.
Figure 5:
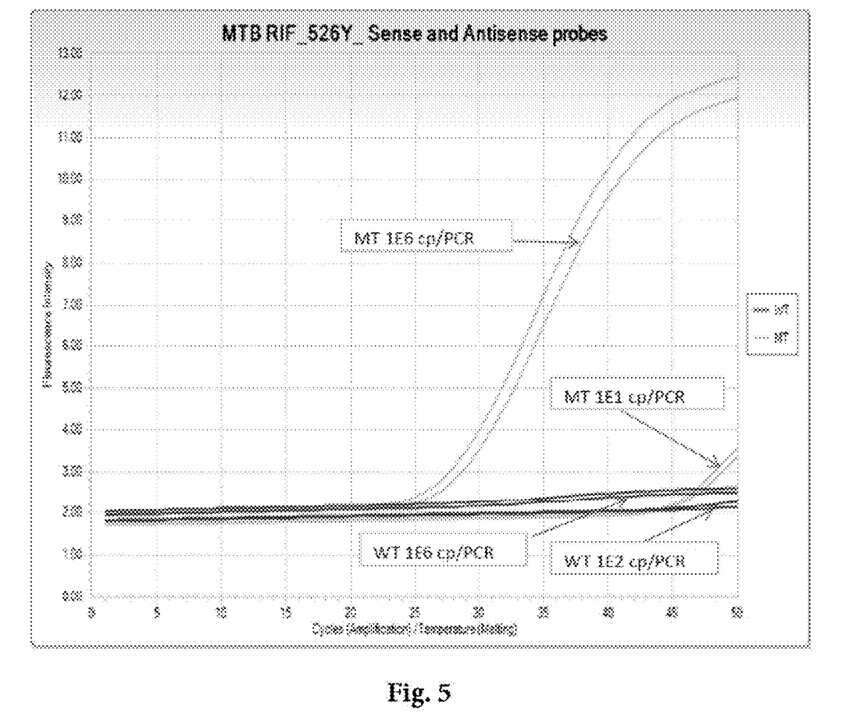
FIG. 5 shows real time PCR amplification curves for wild type and Mutant 526Y SNP detection using a double stranded hydrolysis probe with both sense and antisense probe strands being SNP specific.
Figure 6:
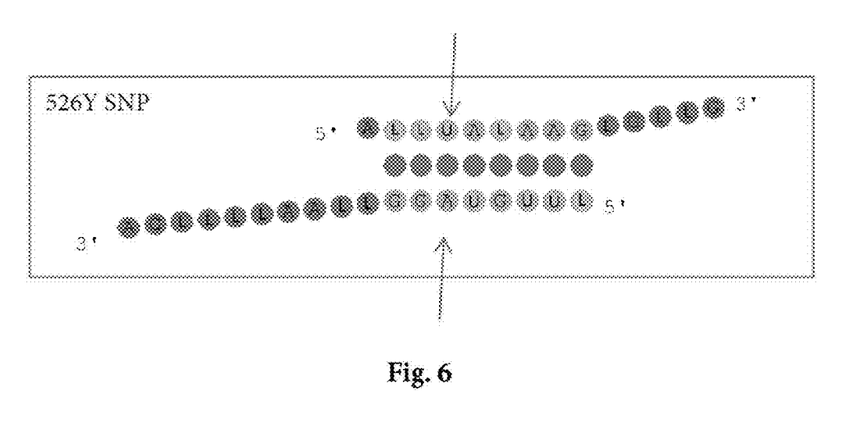
FIG. 6 shows a 526Y SNP specific double stranded hydrolysis probe with both sense and anti-sense probe strands being SNP specific.

Methods, kits, and hydrolysis probes for detecting a single nucleotide polymorphism (SNP) in a target nucleic acid in a sample are described herein. The increased sensitivity of real-time PCR for detection of a SNP in a target nucleic acid compared to other methods, as well as the improved features of real-time PCR including sample containment and real-time detection of the amplified product, make feasible the implementation of this technology for routine diagnosis and detection of a SNP in a target nucleic acid in the clinical laboratory.

The methods may include performing at least one cycling step that includes amplifying one or more portions of a target nucleic acid molecule, e.g., a gene target containing the SNP of interest to be detected, in a sample using a primer including a nucleic acid and another primer including another nucleic acid sequence to produce an amplification product including a sense strand and an anti-sense strand. As used herein, "primer", "primers", and "primer pairs" refer to oligonucleotide primer(s) that specifically anneal to the nucleic acid sequence target, and initiate synthesis therefrom under appropriate conditions. Each of the primers anneal to a region within or adjacent to the respective target nucleic acid molecule such that at least a portion of each amplification product contains nucleic acid sequence corresponding to respective target and SNP, if present. An amplification product is produced provided that the target nucleic acid is present in the sample, whether or not the SNP of interest is present in the target nucleic acid molecule.

The method can also include a hybridizing step that includes providing the amplification product with a double stranded probe including one SNP specific hydrolysis probe including a nucleic acid sequence complementary to a SNP containing region of the sense strand of the amplification product, and another SNP specific hydrolysis probe including another nucleic acid sequence complementary to a SNP containing region of the anti-sense strand of the amplification product. The double stranded SNP specific hydrolysis probes may be completely double stranded across the entire lengths of the sense and the anti-sense stands of the probes, or the double stranded probe may be partially double stranded across a region of the lengths of the sense and the anti-sense strand of the probes. For example, the region where the sense and the anti-sense strands of the double stranded probe form a double stranded region may be, for example, a region toward the 5' end, or the 3' end, or the central area of the sense and the anti-sense strands of the double stranded probe. The double stranded probe should overlap across the area where the SNP of interest is located. Each of the SNP specific hydrolysis probes of the double stranded probe can include a first and a second interactive label, a 5' end and a 3' end. In some embodiments, one hydrolysis probes of the double stranded probe, e.g., the anti-sense probes, can include a hairpin structure toward the 3' end. The hairpin structure can be designed to include a nucleic acid region that is non-naturally occurring which may include one or more changed nucleotides that are not part of the naturally occurring sequence, or may include one or more additional non-naturally occurring nucleotides, which are nucleotides added to the naturally occurring sequence, in order to produce the hairpin structure. In this way, a nucleic acid sequence that does not normally form a hairpin structure at the 3' end can be designed to form a hairpin by, e.g., altering the nucleic acid sequence, for example, changing one or more nucleotides in the sequence toward the 3' end, or by adding one or more nucleotides to the nucleic acid sequence at the 3' end.

In order to detect whether or not the SNP of interest is present or absent in the nucleic acid target in the sample, the amplification product is detected by way of the detectable label being released from both of the first and second SNP specific hydrolysis probes. If the amplification product is detected by way of the double stranded SNP specific hydrolysis probes, the presence of SNP is indicated. If alternatively, the amplification product is not detected by way of the double stranded SNP specific hydrolysis probes, the presence of SNP is not indicated. Thus, the presence of the amplification products (sense and/or anti-sense) is indicative of the presence of the SNP in the target nucleic acid target, and the absence of the amplification products is indicative of the absence of the SNP in the target nucleic acid target.

As used herein, the term "amplifying" refers to the process of synthesizing nucleic acid molecules that are complementary to one or both strands of a template nucleic acid molecule (e.g., target nucleic acid molecules for Human immunodeficiency virus (HIV) or *Mycobacterium tuberculosis* (MTB), or Hepatitis C virus (HCV)). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" is used herein as known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. In general, primers are designed based on known template sequences. One primer primes the sense strand, and the other primes the complementary (anti-sense) strand of the target DNA or cDNA. PCR can be performed on a uniform target DNA or RNA (i.e., targets with the same sequence) or on mixed target DNAs or RNAs, (i.e., targets with different intervening sequences flanked by conserved sequences). For mixed DNAs/RNAs (e.g., containing sequence heterogeneity) even mismatched primers can function in the PCR reaction if the sequences of the targets have enough complementarity to the mismatched primers (i.e., tolerant primers).

The term "hybridizing" refers to the annealing of one or more probes to an amplification product. Hybridization conditions typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides of the present disclosure are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference.

As used herein, the term "non-naturally occurring nucleotide" in the context of the hairpin structure toward the 3' end of the probe as described herein, refers to a nucleotide that is not a naturally occurring nucleotide in the natural sequence, e.g., in the wild type sequence. Such non-naturally occurring nucleotide may be nucleotide that has been changed, for example A to G, or may be an added non-naturally occurring nucleotide, for example a G may be inserted into the sequence. The inclusion of the non-naturally occurring nucleotides can be designed into the natural sequence in order to produce the hairpin structure, in other words, the natural sequence can be engineered to force a hairpin structure where a hairpin structure would not naturally occur. The natural sequence may be designed to include a hairpin structure toward the 3' end by changing or adding at least one non-naturally occurring nucleotide in the natural sequence, for example 1, 2, 3, 4, 5, 6, or 7 non-naturally occurring nucleotides may be included in the natural sequence in order to produce the hairpin structure.

Target Nucleic Acids and Oligonucleotides

The present description provides methods to detect SNP in a target nucleic acid by amplifying, for example, a portion of the target nucleic acid sequences, which may be any target nucleic acid sequence known or suspected to comprise one or more SNPs, for example target nucleic acid sequences from, e.g., HIV, HCV, or MTB that is rifampicin resistant.

For detection of SNP in the target nucleic acid sequence, primers and probes to amplify the target nucleic acid sequences can be prepared. Also, functional variants can be evaluated for specificity and/or sensitivity by those of skill in the art using routine methods. Representative functional variants can include, e.g., one or more deletions, insertions, and/or substitutions in the primers and/or probes disclosed herein. For example, a substantially identical variant of the primers or probes can be provided in which the variant has at least, e.g., 80%, 90%, or 95% sequence identity to one original primers and probes, or a complement thereof.

A functionally active variant of any of primer and/or probe may be identified which provides a similar or higher specificity and sensitivity in the presently described methods, kits, or hydrolysis probes as compared to the respective original sequences.

As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify the target nucleic acid sequences can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the present methods may use double stranded probes in order to detect the presence or absence of SNP in a target nucleic acid sequence. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids". A "probe" can be referred to as a "detection probe" meaning that it detects the target nucleic acid.

In some embodiments, the described probes can be labeled with at least one fluorescent label. In one embodiment probes can be labeled with a donor fluorescent moiety, e.g., a fluorescent dye, and a corresponding acceptor fluorescent moiety, e.g., a quencher.

Designing oligonucleotides to be used as TaqMan hydrolysis probes can be performed in a manner similar to the design of primers. Embodiments of the present disclosure may use a double stranded probe for detection of the amplification product. Depending on the embodiment, the probe may include at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 30 (e.g., 16, 18, 20, 21, 22, 23, 24, or 25) nucleotides in length.

Polymerase Chain Reaction (PCR)

U.S. Pat. Nos. 4,683,202; 4,683,195; 4,800,159; and 4,965,188 disdose conventional PCR techniques. U.S. Pat. Nos. 5,210,015; 5,487,972; 5,804,375; 5,804,375; 6,214,979; and 7,141,377 disdose real-time PCR and TaqMan® techniques. PCR typically employs two oligonucleotide primers that bind to a selected nucleic acid template (e.g., DNA or RNA). Primers useful in the described embodiments include oligonucleotides capable of acting as points of initiation of nucleic acid synthesis within the target nucleic acid sequences. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the target nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ target nucleic acid such as RNA or DNA (cDNA). The template nucleic acid need not be purified; it may be a minor fraction of a complex mixture, such as target nucleic acid contained in human cells. Target nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, a oligonucleotide probe can contain a donor fluorescent moiety and a corresponding quencher, which may or not be fluorescent, and which dissipates the transferred energy in a form other than light. When the probe is intact, energy transfer typically occurs between the two fluorescent moieties such that fluorescent emission from the donor fluorescent moiety is quenched. During an extension step of a polymerase chain reaction, a probe bound to an amplification product is cleaved by the 5' to 3' nuclease activity of, e.g., a Taq polymerase such that the fluorescent emission of the donor fluorescent moiety is no longer quenched. Exemplary probes for this purpose are described in, e.g., U.S. Pat. Nos. 5,210,015; 5,994,056; and 6,171,785. Commonly used donor-acceptor pairs include the FAM-TAMRA pair. Commonly used quenchers are DABCYL and TAMRA. Commonly used dark quenchers include Black-Hole Quenchers™ (BHQ), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine×isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present disclosure is the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide which contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of a SNP in a Target Nucleic Acid

The present disclosure provides methods for detecting the presence or absence of a SNP in a target nucleic acid in a biological. Methods provided avoid problems of sample contamination, false negatives, and false positives. The methods include performing at least one cycling step that includes amplifying a portion of the target nucleic acid molecule from a sample using a primer pair, and a fluorescent detecting step utilizing double stranded SNP specific hydrolysis probes wherein in some embodiments one strand of the double stranded probes includes a hairpin structure toward the 3' end. Multiple cycling steps may be performed, preferably in a thermocycler. The described methods can be performed using the primers and probes to detect the presence of the SNP in a target nucleic acid in the sample.

As described herein, amplification products can be detected using labeled hybridization hydrolysis probes that take advantage of FRET technology. One FRET format utilizes TaqMan® technology to detect the presence or absence of an amplification product, and hence, the presence or absence of the target nucleic acid. TaqMan® technology utilizes one single-stranded hybridization hydrolysis probe labeled with, e.g., one fluorescent dye and one quencher, which may or may not be fluorescent. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of the target nucleic acid in the sample.

Generally, the presence of FRET indicates the presence of the SNP in a target nucleic acid in the sample, and the absence of FRET indicates the absence of the SNP in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of the presence of an SNP in a target nucleic acid in a sample.

Representative biological samples that can be used in practicing the methods of the present disclosure include, but are not limited to dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release target nucleic acid or in some cases, the biological sample can be contacted directly with the PCR reaction components and the appropriate oligonucleotides.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996; 5,683,896; and U.S. Pat. No. 5,945,313 to reduce or eliminate contamination between one thermocycler run and the next.

Conventional PCR methods in conjunction with FRET technology can be used to practice the methods of the present disclosure. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

It is understood that the embodiments of the present disclosure are not limited by the configuration of one or more commercially available instruments.

Articles of Manufacture/Kits

The present disclosure further provides for articles of manufacture or kits to detect a SNP in a target nucleic acid. An article of manufacture can include primers and double stranded probes used to detect the SNP as described herein, together with suitable packaging materials. Representative primers and probes for detection of the SNP are capable of hybridizing to the target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to a SNP in a target nucleic acid target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the SNP specific probes. Examples of suitable FRET donor fluorescent moieties and corresponding acceptor fluorescent moieties are provided above.

Articles of manufacture can also contain a package insert or package label having instructions thereon for using the primers and probes to detect a SNP in a target nucleic acid in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the disclosed subject matter will be further described in the following examples, which do not limit the scope of the invention described in the claims.

EXAMPLES

The following examples and figures are provided to aid the understanding of the present invention, the true scope of which is set forth in the appended claims. It is understood that modifications can be made in the procedures set forth without departing from the spirit of the invention.

Example I

MTB-RIF TaqMan® SNP Detection

Tuberculosis (TB) is a serious lung disorder commonly caused by *Mycobacterium tuberculosis* (MTB) or other members of the MTB-complex. Drug-resistant strains of MTB are on the rise and a particularly dangerous form of drug-resistant tuberculosis is multidrug-resistant tuberculosis (MDR-TB). MDR-TB is defined as MTB that has developed resistance to at least two of the most commonly used anti-tuberculosis drugs, rifampicin and isoniazid. Approximately 83-87% of the rifampicin resistance is caused by single nucleotide polymorphism within the 81 base pair Rifampicin Resistance Determining Region (RRDR) of the rpoB gene encoding the β-subunit of RNA polymerase.

Mutant specific double stranded TaqMan® hydrolysis probes were designed with a fluorophore at the 5' end and an internal quencher for each probe strands. Each of the sense and anti-sense strands of the probes were designed to be SNP specific, i.e., being perfectly matched with the sense and anti-sense mutant version of target containing the SNP of interest, and being similarly mismatched with the wild type version of the target. In addition, in some embodiments additional base/bases were introduced at the 3' end of the probe that would result in a hairpin structure towards the 3' end. Probes were designed so that the mismatch between the WT and MT lies between the reporter and the quencher near the 5' end on each strand of the probes. When the TaqMan® probe is intact, the reporter and quencher stay close to each other, which prevent the emission of any fluorescence.

The primer and TaqMan® probe anneal to the complementary DNA strand following denaturation during PCR. After hybridization and during the extension phase of PCR, the 5' to 3' nuclease activity of the DNA polymerase cleaves the probe which separates reporter and quencher dyes and fluorescence is detected. In those embodiments which include the hairpin structure, the hairpin structure near the 3' end of the probe delays the hybridization of the 3' half of the probe to the template and thus helps in the discrimination of the WT and the MT target based on the single base pair difference or mismatch. The 5' half of the MT hairpin TaqMan® probe will hybridize more efficiently to the MT plasmid DNA template as compared to the WT template. When the MT specific probe finds the WT target, the single mismatch to the WT target will prevent hybridization and probe cleavage and little or no fluorescence is detected.

Materials and Methods

DNA Target—Wild-Type (WT) and Mutant (MT) Plasmids

MT and WT plasmid DNA: tested inputs ranging from 1e6 cp/PCR to 10 cp/PCR shown in Table I showing a portion of the Rifampicin Resistance Determining Region (RRDR) of the rpoB gene in *Mycobacterium tuberculosis*.

TABLE I

Wildtype and Mutant Plasmid DNA

| SEQ ID NO | | SEQUENCE |
|---|---|---|
| 7 | MT Plasmid with 526N SNP | GCCAGCTGAGCCAATTCATGGTCCAGAAC AACCCGCTGTCGGGGTTGACCAACAAGCG CCGACTGTCGGCGCTGGGGTCCGGCGG |
| 8 | MT Plasmid for 531L SNP | GCCAGCTGAGCCTATTCATGGACCAGAAC AACCCGCTGCAGGGGTTGACCCACAAGCG CCGACTGTTGGCGCTGGGGCCCGGCGG |
| 9 | MT Plasmid with 526Y SNP | GCCAGCTGAGCCAATTCATGGACCAGAAC AACCCGCTGTCGGGGTTGACCCACAAGCG CCGACTGTCGGCGCTGGGGCCCGGCGG |
| 10 | WT Plasmid | GCCAGCTGAGCCAATTCATGGACCAGAAC AACCCGCTGTCGGGGTTGACCCACAAGCG CCGACTGTCGGCGCTGGGGCCCGGCGG |

MTB specific oligonucleotides: One set of forward and reverse primers for both wild-type and mutant plasmids Mutant specific double stranded TaqMan® probes shown in Table II

TABLE II

Sense and Antisense SNP Specific Probes

| SEQ ID NO | | SEQUENCE |
|---|---|---|
| 1 | Probe (526N SNP) - Sense | 5'-EALLAAQLAAGLGLLGALP-3' |
| 2 | Probe (526N SNP) with 3' hairpin - Antisense | 5'-ETTGTTGQGTCAACCCCG ACGGGGP-3' |
| 3 | Probe (531L SNP)-Sense | 5'-EALUGUUQGGLGLUGGP-3' |

TABLE II -continued

| Sense and Antisense SNP Specific Probes | | |
|---|---|---|
| SEQ ID NO | | SEQUENCE |
| 4 | Probe (531L SNP)-Antisense | 5'-ELLAALAQGTLGGLGLP-3' |
| 5 | Probe (526Y SNP)-Sense | 5'-EALLUALQAAGLGLLGP-3' |
| 6 | Probe (526Y SNP)-Antisense | 5'-ELUUGUAQGGLLAALLLGAP-3' |

Designations: E stands for Threo-HEX; P stands for Phosphate; Q stands for BHQ-2 quencher; L stands for Propynyl dC; U stands for Propynyl dU; double underlined letters are the site of the SNPs; and bolded underlined letters are bases that are changed or added to form hairpin.

Platforms: LightCyder® 480 System

Real time PCR amplifications were performed using a set of forward and reverse primers and double stranded SNP specific TaqMan® probes. Wild-type or Mutant plasmid DNA was tested at 1e6, 1e2, 1e3 and 1e1 cp/PCR. The PCR reaction volume was 50 uL, and the master mix components and thermoprofile conditions are listed below. The amplifications were performed on the LC480 platform and the PCR growth curves were analyzed using the ATF data analysis software. Results are shown in FIGS. 1 through 6.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A kit for detecting a single nucleotide polymorphism (SNP) that generates a mutant version of a target nucleic acid in a sample, comprising:
  a first primer comprising a first nucleic acid sequence and a second primer comprising a second nucleic acid sequence specific to produce an amplification product comprising a sense strand and an anti-sense strand of the target nucleic acid; and
  a double stranded probe comprising:
    a first mutant specific hydrolysis probe comprising a third nucleic acid sequence complementary to a region of the sense strand that contains the mutant generating SNP, the first mutant specific hydrolysis probe comprising a first interactive label and a second interactive label, a first 5' end and a first 3' end; and
    a second mutant specific hydrolysis probe comprising a fourth nucleic acid sequence complementary to a region of the anti-sense strand that contains the mutant generating SNP, the second mutant specific hydrolysis probe comprising a third interactive label and a fourth interactive label, a second 5' end and a second 3' end;
  wherein the target nucleic acid is the rpoB gene in *Mycobacterium tuberculosis*.

2. The kit of claim 1, wherein the second mutant specific hydrolysis probe comprises a hairpin structure toward the second 3' end, the hairpin structure comprising a region of non-naturally occurring nucleic acid sequence by changing or adding at least one non-naturally occurring nucleotide into a naturally occurring sequence.

3. The kit of claim 2, wherein the first interactive label comprises a first donor fluorescent moiety at the first 5' terminus, and the second interactive label comprises a first corresponding acceptor fluorescent moiety within no more than 8 nucleotides of the first donor fluorescent moiety on the first mutant specific hydrolysis probe, and wherein the third interactive label comprises a second donor fluorescent moiety at the second 5' terminus, and the fourth interactive label comprises a second corresponding acceptor fluorescent moiety within no more than 8 nucleotides of the second donor fluorescent moiety on the second mutant specific hydrolysis probe.

4. The kit of claim 2, wherein the first acceptor fluorescent moiety is a first quencher, and wherein the second acceptor fluorescent moiety is a second quencher.

5. The kit of claim 1, further comprising a polymerase enzyme having 5' to 3' nuclease activity.

6. The kit of claim 1, wherein the first and second nucleic acid sequences of the primers and/or the third and fourth nucleic acid sequences of the hydrolysis probes comprise at least one modified nucleotide.

7. The kit of claim 1, wherein the first and second nucleic acid sequences of the primers and/or the third and fourth nucleic acid sequences of the hydrolysis probes have 40 or fewer nucleotides.

8. The kit of claim 1, wherein the double stranded probe comprises a pair of oligonucleotides with nucleotide sequences selected from the group consisting of SEQ ID NO:1 and SEQ ID NO:2; SEQ ID NO:3 and SEQ ID NO:4; and SEQ ID NO:5 and SEQ ID NO:6.

9. A double stranded probe configured to detect a single nucleotide polymorphism (SNP) that generates a mutant version of a target nucleic acid, the double stranded probe comprising:
   a first mutant specific hydrolysis probe comprising a first nucleic acid sequence complementary to a mutant generating SNP-containing region of a sense strand of the target nucleic acid, the first mutant specific hydrolysis probe comprising a first interactive label and a second interactive label, a first 5' end and a first 3' end; and
   a second mutant specific hydrolysis probe comprising a second nucleic acid sequence complementary to a mutant generating containing region of an anti-sense strand of the target nucleic acid, the second SNP mutant specific hydrolysis probe comprising a third interactive label and a fourth interactive label, a second 5' end and a second 3' end;
   wherein the target nucleic acid is the rpoB gene in *Mycobacterium tuberculosis*.

10. The double stranded probe of claim 9, wherein the second mutant specific hydrolysis probe comprises a hairpin structure toward the second 3' end, the hairpin structure comprising a region of non-naturally occurring nucleic acid sequence by changing or adding at least one non-naturally occurring nucleotide into a naturally occurring sequence.

11. The double stranded probe of claim 10, wherein the first interactive label comprises a first donor fluorescent moiety at the first 5' terminus, and the second interactive label comprises a first corresponding acceptor fluorescent moiety within no more than 8 nucleotides of the first donor fluorescent moiety on the first mutant specific hydrolysis probe, and wherein the third interactive label comprises a second donor fluorescent moiety at the second 5' terminus, and the fourth interactive label comprises a second corresponding acceptor fluorescent moiety within no more than 8 nucleotides of the second donor fluorescent moiety on the second mutant specific hydrolysis probe.

12. The double stranded probe of claim 10, wherein the first acceptor fluorescent moiety is a first quencher, and wherein the second acceptor fluorescent moiety is a second quencher.

13. The double stranded probe of claim 9, wherein first and second nucleic acid sequences of the hydrolysis probes comprise at least one modified nucleotide.

14. The double stranded probe of claim 9, wherein the first and second nucleic acid sequences of the hydrolysis probes have 40 or fewer nucleotides.

15. The double stranded probe of claim 9 comprising a pair of oligonucleotides with nucleotide sequences selected from the group consisting of SEQ ID NO:1 and SEQ ID NO:2; SEQ ID NO:3 and SEQ ID NO:4; and SEQ ID NO:5 and SEQ ID NO:6.

* * * * *